(12) United States Patent
Gaeta

(10) Patent No.: US 11,382,551 B2
(45) Date of Patent: Jul. 12, 2022

(54) ELECTRODE PAIRING FOR IMPROVED BIPOLAR ELECTROGRAM RECORDING IN ELECTROPHYSIOLOGY

(71) Applicant: Duke University, Durham, NC (US)

(72) Inventor: Stephen Gaeta, McLean, VA (US)

(73) Assignee: Duke University, Durham, NC (US)

( * ) Notice: Subject to any disclaimer, the term of this patent is extended or adjusted under 35 U.S.C. 154(b) by 212 days.

(21) Appl. No.: 16/867,065

(22) Filed: May 5, 2020

(65) Prior Publication Data
US 2020/0352465 A1   Nov. 12, 2020

Related U.S. Application Data

(60) Provisional application No. 62/844,397, filed on May 7, 2019.

(51) Int. Cl.
  *A61B 5/333* (2021.01)
  *A61B 5/287* (2021.01)
  *A61B 5/367* (2021.01)

(52) U.S. Cl.
  CPC .......... *A61B 5/287* (2021.01); *A61B 5/333* (2021.01); *A61B 5/367* (2021.01)

(58) Field of Classification Search
  CPC .......... A61B 5/367; A61B 2018/00839; A61B 2018/00654
  See application file for complete search history.

(56) References Cited

U.S. PATENT DOCUMENTS

2018/0296108 A1* 10/2018 Stewart .............. A61B 5/349
2019/0223744 A1*  7/2019 Cheng ................ A61B 5/283

* cited by examiner

*Primary Examiner* — George R Evanisko
(74) *Attorney, Agent, or Firm* — Michael Best & Friedrich LLP

(57) ABSTRACT

Systems and methods for recording bipolar electrogram signals by dynamically selecting electrode pairs. For a particular electrode of interest, a reference electrode is identified as the physically closest electrode to the electrode of interest that satisfies at least one selection criterion indicative of an absence of concurrent electrical activation.

20 Claims, 4 Drawing Sheets

ELECTRODE PAIRING FOR IMPROVED BIPOLAR ELECTROGRAM RECORDING IN ELECTROPHYSIOLOGY

RELATED APPLICATIONS

This application claims the benefit of U.S. Provisional Patent Application No. 62/844,397, filed May 7, 2019 and entitled "SYSTEMS AND METHODS FOR IMPROVING BIPOLAR ELECTROGRAM RECORDINGS IN ELECTROPHYSIOLOGY," the entire contents of which are incorporated herein by reference.

BACKGROUND

The present invention relates to systems and methods for recording and monitoring electrogram data in electrophysiology.

SUMMARY

In clinical electrophysiology, electrical potential differences are measured (or calculated) between two electrodes. The features of the resulting time-resolved electrical potential ("electrogram" or EGM) can then be used, for example, to guide ablation procedure aimed at curing or preventing cardiac arrhythmia. In some implementations, a plurality of electrodes are positioned at different locations on a patients anatomy (e.g., on a tissue surface). The signals recorded from each individual electrode are referred to herein as "unipolar" electrograms. In a unipolar electrogram, a potential difference is measured between a particular electrode (i.e., an "electrode of interest") and a second electrode (i.e., a "reference electrode"). In some implementations, the reference electrode may be a physical electrode positioned at a location distant from the electrode of interest (i.e., an "indifferent electrode" (U0)). In other implementations, the reference electrode is an artificially constructed reference such as "Wilson's Central Terminal" (WCT). The timing of local activation for any electrode can be determined by its so-called "unipolar EGM" which represents the potential difference between the electrode and the reference electrode (e.g., the "indifferent" electrode).

A "bipolar" electrogram refers to a signal difference between two electrodes. In some cases, the electrical signal of a bipolar electrogram is presumed to represent more localized electrical activity than unipolar electrograms because the bipolar electrogram is indicative of electrical activity in the local tissue under the two recording electrodes. Features of a bipolar electrogram can also be used, for example, to guide ablation procedures in addition to or instead of data from the unipolar electrogram(s). Also, because a bipolar electrogram represents a "difference" between the signals from two electrodes, the bipolar electrogram provides rejection of far field signals and common mode noise shared by both electrodes. A bipolar electrogram can be calculated by subtracting a unipolar electrogram of one electrode from that of another (e.g., adjacent) electrode. A bipolar electrogram can also be measured directly by measuring the potential difference between the two electrodes.

However, with closely spaced electrode pairs, the possibility arises that the calculated bipolar voltage amplitude will be affected by simultaneous electrical activity on both poles. In this case, the second electrode is not a true "indifferent" electrode and will impart important information into the resulting bipolar electrogram. This will impact the ability of the resulting bipolar EGM features to accurately represent underlying tissue properties. For example, the bipolar EGM amplitude of a closely spaced electrode pair will be affected by its angle of orientation relative to a propagating wave-front (so-called "directional sensitivity").

In various implementations, the methods and systems presented in this disclosure provide techniques for improving bipolar electrogram recording in electrophysiology. In some implementations, the optimal electrode pairs (for example, two electrodes on a multielectrode catheter and/or electrodes on two different catheters) are dynamically assigned for use together in bipolar EGM calculations so as to avoid unwanted effects such as those described above.

In one embodiment, the invention provides a method for recording a bipolar electrogram. An electrode of interest is selected from a plurality of electrodes that are positioned to detect local electrical activity at each of a plurality of different tissue locations. A second electrode is then selected from the plurality of electrodes as a bipolar electrogram reference electrode for the electrode of interest. The second electrode is selected by identifying the closest electrode to the electrode of interest that satisfies at least one selection criterion indicating an absence of concurrent electrical activation with the electrode of interest. A bipolar electrogram for the electrode of interest is then recorded based on an electrical potential difference between the electrode of interest and the selected second electrode.

In another embodiment, the invention provides a bipolar electrogram recording system that includes a plurality of electrodes and an electronic controller. The plurality of electrodes are positionable to detect local electrical activity at each of a plurality of different tissue locations. The electronic controller is configured to select an electrode of interest from the plurality of electrodes and to select a second electrode from the plurality of electrodes to serve as the bipolar electrogram reference electrode for the electrode of interest. The electronic controller is configured to select the second electrode from the plurality of electrodes by identifying the closest electrode to the electrode of interest that satisfies at least one selection criterion indicating an absence of concurrent electrical activation with the electrode of interest. The electronic controller then records a bipolar electrogram for the electrode of interest based on an electrical potential difference between the electrode of interest and the selected second electrode.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
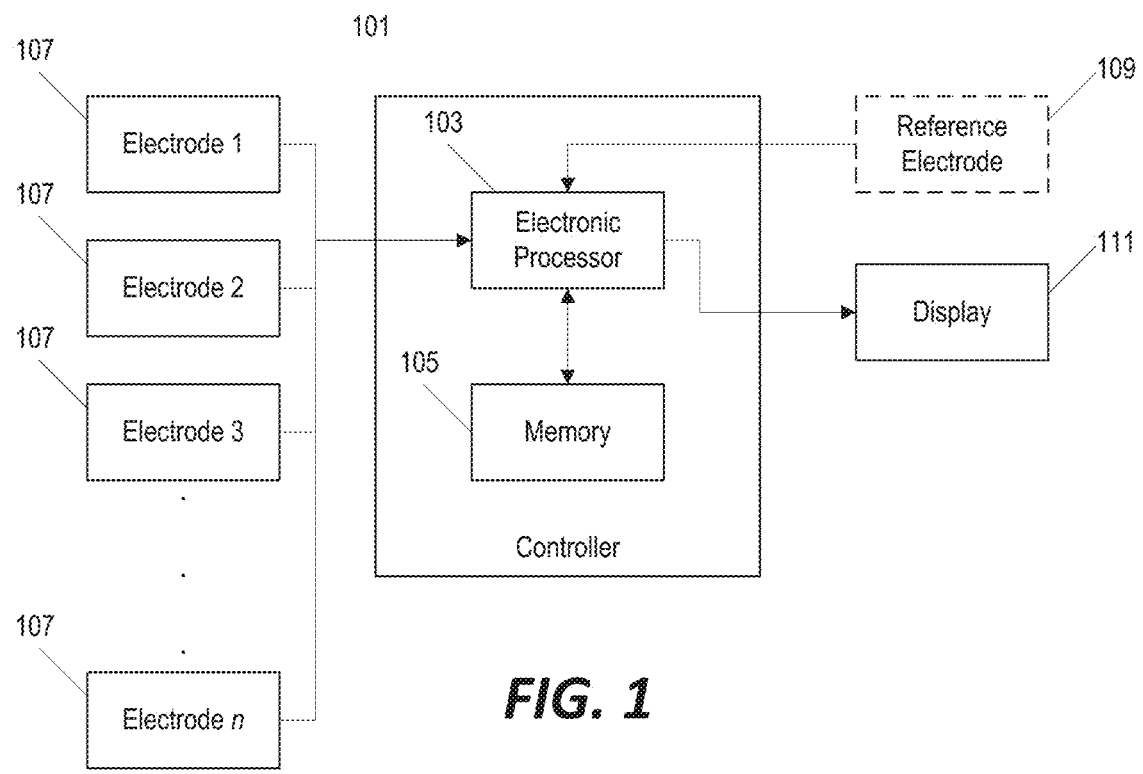
FIG. 1 is a block diagram of a system for recording electrogram data.

FIG. 1 illustrates an example of a system for measuring and recording electrogram data. The system includes a controller 101 with an electronic processor 103 and a non-transitory computer-readable memory 105. The memory 105 is communicatively coupled to the electronic processor 103 and stores data (e.g., recorded electrogram data). The memory 105 also stores computer-executable instructions that are accessed and executed by the electronic processor 103 to provide the functionality of the controller 101 (including, for example, the functionality described herein). The controller 101 may be provided in a number of different ways in various different implementations. In some implementations, the controller 101 is provided as part of an application-specific integrated circuit specifically designed for and housed internally by an electrogram monitoring/recording system. In other implementations, the controlled 101 is provided, for example, as a desktop computer or tablet computer. Furthermore, also the system of FIG. 1 shows only a single controller 101 with a single electronic processor 103 and memory 105, in some implementations, the system functionality may be provided by multiple different controllers, processors, and/or memory modules.

In the example of FIG. 1, the controller 101 is communicatively coupled to a plurality of electrodes 107. In various different implementations, the plurality of electrodes 107 may be provided as electrodes arranged on a single electrode catheter, multiple electrode catheters, and/or separate individual electrodes. The electrodes 107 may be communicatively coupled to the controller 101 by a wired and/or wireless communication interface(s). In some implementations, the controller 101 is also communicatively coupled to one or more reference electrodes 109. The reference electrode 109 may be an electrode included in the same electrode catheter as the other sensing electrodes 107 or may be a separate electrode for internal or external positioning. For example, in some implementations, the electrodes 107 may be provided as an electrode catheter that is internally positionable such that the individual electrodes 107 contact surfaces of cardiac tissue. In some such cases, the reference electrode(s) 109 may be separate electrodes positioned on an external skin surface of the same patient. For example, when using the Wilson's Central Terminal (WCT) for unipolar electrograms, the reference electrode 109 may include multiple separate electrodes that are positioned on the skin surface of the patient near the limbs (e.g., the right arm, left arm, right leg, and/left leg of the patient). However, in some other implementations, the system may be configured to use one or more of the electrodes 107 as the "reference electrodes" and, therefore, in some such implementations, a separate dedicated "reference electrode" might not be included.

As described in further detail below, the controller 101 is configured to detect and record unipolar and/or bipolar electrogram data from the electrodes 107. In some implementations, the controller 101 is configured to selectively record unipolar electrogram data from one or more of the electrodes 107 and to calculate bipolar electrograms based on multiple unipolar electrograms. Additionally or alternatively, in some implementations, the controller 101 is configured to directly measure bipolar electrograms by selectively identifying two electrodes 107 and monitoring/recording the potential difference between the identified electrode pair.

In the example of FIG. 1, the controller 101 is also communicatively coupled to a display 111. In some implementations, the controller 101 is configured to transmit signals and/or data to the display 111 to cause the display 111 to output information regarding the recorded EGM data and/or system operation to a user. In some implementations, the display 111 may include a graphical display screen configured to output graphical and/or textual information based on signals/data received form the controller. In some implementations, the display 111 may also be provided as a graphical user interface through which a user is able to control the operation of the system and/or adjust how the recorded data is shown on the display (i.e., the user may be able to select a particular electrode of interest through the user interface). In other implementations, the controller 101 may be communicatively coupled or selectively couplable to a different type of user interface in addition to or instead of the graphical user interface provided by display 111.

Figure 2:
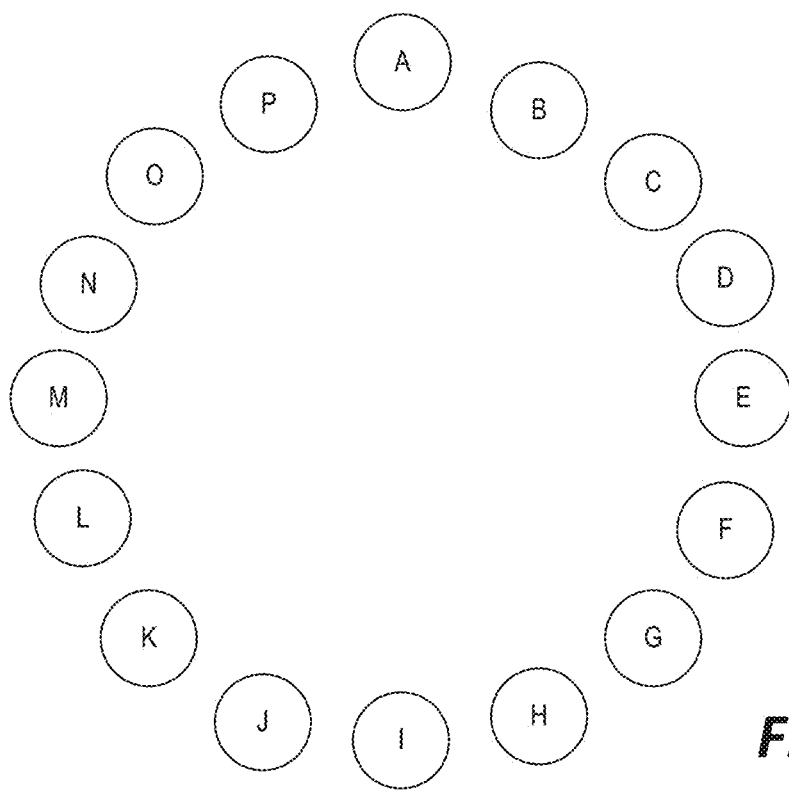
FIG. 2 is a schematic diagram of a first example of an electrode arrangement for use in the system of FIG. 1.

FIG. 2 illustrates one example of an arrangement of electrodes 107 in an electrode catheter. In this example, the electrode catheter includes 16 electrodes (labelled "A" through "F") arranged in a ring. However, in other implementations, the electrodes on an electrode catheter may be arranged differently (e.g., a linear array of electrodes, a electrodes "branching" from a central catheter stem, etc.). In some implementations, the electrode catheter is through the femoral vein into the right ventricle of the heart. The arrangement of the electrodes and the placement of the electrode catheter causes each individual electrodes to contact the cardiac tissue at a different location. However, again, in other implementations, the electrode catheter may be inserted and positioned differently and may be adapted to electrically monitor tissues other than the heart.

As described above, the unipolar electrogram of each individual electrode in the ring-shaped array of FIG. 2 can be recorded by measuring a different in electrical potential between an individual electrode and a reference (e.g., a dedicated reference electrode). A bipolar electrogram can also be recorded for each individual electrode by calculating or directly measuring a potential difference between the electrode of interest and another electrode in the array. In some implementations, the system (e.g., the system of FIG. 1) is configured to select a second electrode to use as the "reference electrode" for a bipolar electrogram of the electrode of interest by identifying the electrode in the array that is physically closest to the electrode of interest and that does not have concurrent electrical activation. The local activation time of each electrode can be determined by analysis of its unipolar EGM and, in some implementations, the concurrent electrical activation can be defined by unipolar EGM amplitude above a chosen threshold, electrical activation within a fixed time period surround the measured local activation, and/or other techniques for determining EGM signal duration and/or local activity.

Figure 3:
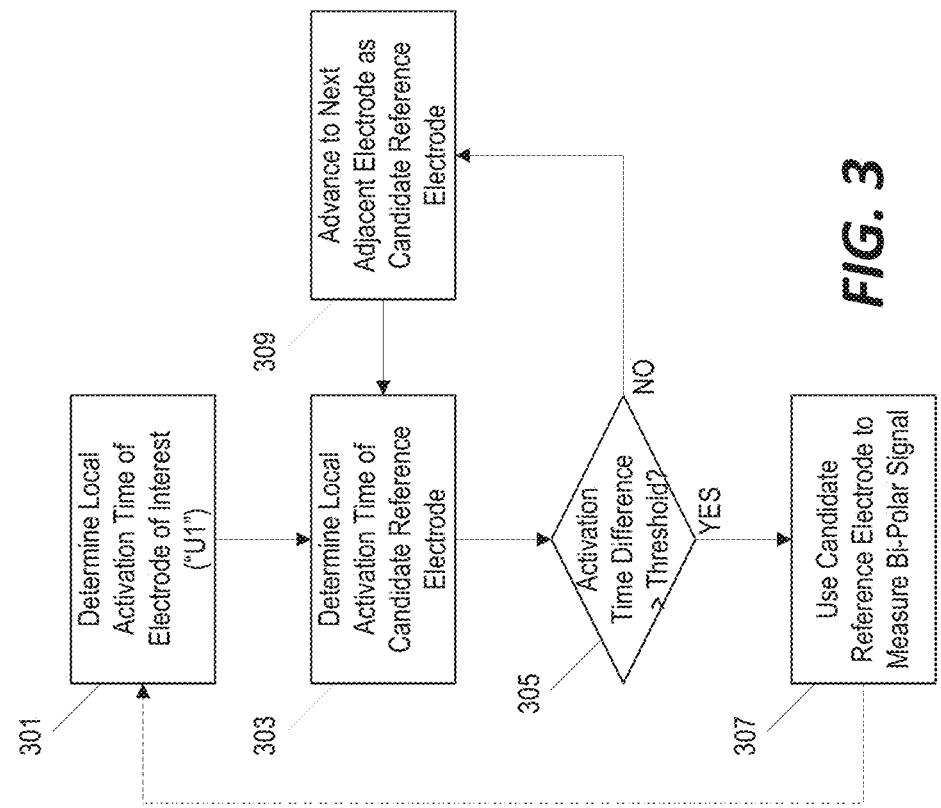
FIG. 3 is a flowchart of a method performed by the system of FIG. 1 for selecting an electrode pair for bipolar electrogram recording based on local activation time.

FIG. 3 illustrates an example of a method executed by the controller 101 of FIG. 1 for selecting a reference electrode for use in recording/calculating a bipolar electrogram by comparing local activation times between the different electrodes. First, the controller 101 determines a local activation time for an electrode of interest ("U1") (step 301). For example, if electrode "A" in the electrode catheter of FIG. 2 is the "electrode of interest," the controller 101 may be configured to determine the local activation time of electrode "A" by analyzing the unipolar electrogram for electrode "A" and identifying a time at which the unipolar electrogram signal exceeds an activation threshold.

As noted above, the reference electrode that will be used to record a bipolar electrogram for electrode "A" will be the closest electrode in the array that does not exhibit concurrent electrical activation with electrode "A." In some implementations, this first "candidate" reference electrode (and the sequence in which subsequent candidate reference electrodes will be considered) is selected based on a known geometry of the electrode catheter and/or known information about the placement of the electrodes. In reference to the example of FIG. 2, the first candidate reference electrode for recording a bipolar electrogram of electrode "A" would be electrode "B" or electrode "P." After a candidate reference electrode is identified based on physical positioning of the electrodes, the controller 101 determines a local activation time of the candidate reference electrode (step 303) and compares it to the local activation time of the electrode of interest (step 305). If the difference between the local activation time of the candidate reference electrode and the electrode of interest is greater than a threshold (step 305), then the candidate reference electrode is used to calculate or measure the bipolar electrogram for the electrode of interest (step 307). However, if the difference between the local activation times is not greater than the threshold (step 305), then the controller 101 advances to the next closest electrode (step 309) and determines whether its local activation time is sufficiently different from the local activation time of the electrode of interest. This process is repeated until a candidate reference electrode is identified with a sufficiently different local activation time (i.e., where a difference between a local activation time of the candidate reference electrode and the local activation time of the electrode of interest exceeds the time threshold).

In some implementations, the method of FIG. 3 is repeated for each of a plurality of different electrodes as the "electrode of interest" in order to record bipolar electrograms for each different electrode. Furthermore, in some implementations and/or in some situations (particularly in situations in which the conduction velocity is subject to change), the process of FIG. 3 may be repeated for the same electrode of interest to determine whether the same "reference electrode" is still suitable for use in determining the bipolar electrogram for the electrode of interest.

Figure 4:
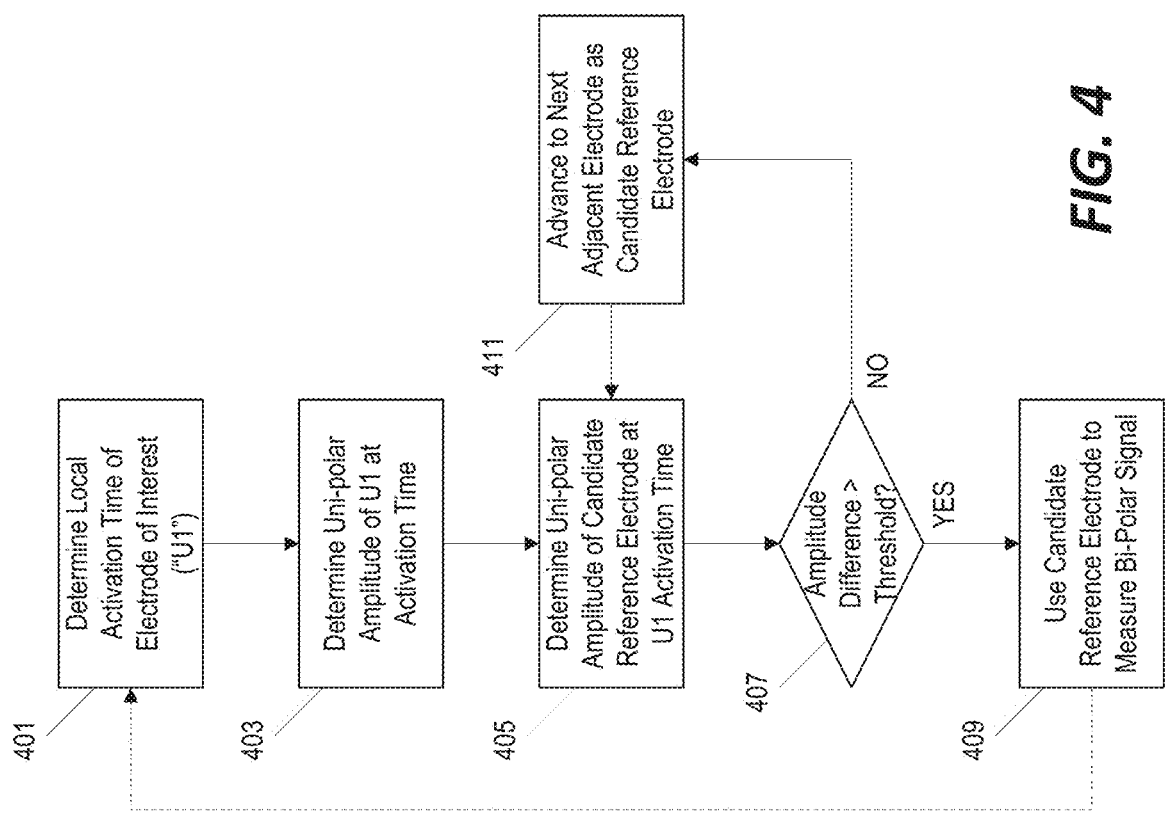
FIG. 4 is a flowchart of another method performed by the system of FIG. 1 for selecting an electrode pair for bipolar electrogram recording based on signal amplitude.

FIG. 4 illustrates another method for identifying a "reference" electrode that is suitable for use in recording a bipolar electrogram for a particular electrode of interest based on relative electrical activity at the local activation time of the electrode of interest. The controller 101 begins by determining the local activation time of the electrode of interest ("U1") (step 401) and determines the unipolar signal amplitude of the electrode of interest at its local activation time (step 403). The controller 101 also determines a unipolar signal amplitude of the first candidate reference electrode at the local activation time of the electrode of interest (step 405) and calculates a difference between the amplitude of the candidate reference electrode and the amplitude of the electrode of interest. A difference in amplitude at the time of local activation is indicative of a lack of concurrent electrical activation at the locations of the two electrodes. Therefore, if the amplitude difference exceeds a defined or determined amplitude threshold (step 407), then the controller 101 will use that candidate reference electrode in recording the bipolar electrogram signal for the electrode of interest (step 409). If not, then the controller 101 will advance to the next closest electrode to evaluate as the next candidate reference electrode (step 411).

In the example of FIG. 4, the controller 101 is configured to evaluate a candidate reference electrode based on a difference in signal amplitude at a particular time (i.e., at the time of local activation of the electrode of interest). However, in some implementations, the controller 101 may be configured to analyze other criteria based on signal amplitude in addition to or instead of amplitude difference in other to evaluate a particular electrodes suitability for use as a bipolar electrogram reference electrode. For example, in some implementations, the controller 101 may be configured to compare the signal amplitude of the candidate reference electrode alone to an amplitude threshold at the local activation time for the electrode of interest and to disqualify the candidate as a bipolar electrogram reference electrode if its unipolar amplitude exceeds the threshold at the local activation time of the electrode of interest. In other implementations, the controller 101 may be configured to eliminate a candidate reference electrode if its unipolar signal amplitude exceeds a threshold at any time over a defined duration. For example, the unipolar signal of the electrode of interest may be evaluated to determine a local activation period (i.e., the duration of time after local activation begins during which the propagating wave is measurable in the unipolar electrogram signal of the electrode of interest) and the controller 101 may be configured to eliminate an electrode as a candidate reference electrode if its unipolar electrogram signal exceeds a defined or determined threshold during the local activation period of the electrode of interest.

Similarly, in some implementations, the method of FIG. 4 may be used instead of or in addition to the method of FIG. 3 (for example, the electrode that is selected as the reference electrode for recording a bipolar electrogram will be the physically closest electrode that satisfies the selection criteria of both FIGS. 3 and 4). Furthermore, the mechanisms described in reference to FIGS. 3 and 4 for evaluating whether a candidate electrode can be used as a reference electrode for a bipolar electrogram utilize a "threshold" for the determination (i.e., a time threshold between local activations or a signal amplitude threshold). In some implementations, the thresholds for the evaluation criteria/criterion may be pre-defined while, in other implementations, the controller 101 may be configured to determined and/or adjust the threshold(s) based, for example, on observer signal data. For example, if the controller is configured to evaluate a candidate electrode based on local activation times, it may also be configured to adjust the time threshold based on measured characteristics such as, for example, an observed signal duration.

In some implementations, the controller 101 may be configured to being with the physically closest electrode as the first candidate reference electrode. However, in some implementations, additional criteria—such as, for example, physical distances between electrodes and/or other known or measured information—can be used to reduce the number of electrodes in the "candidate pool" of electrodes even before analyzing the unipolar signal data from each potential candidate electrode. In the ring-shaped electrode array of FIG. 2, the controller 101 may be configured to begin with either electrode "B" or electrode "P" as its first candidate for use as a bipolar EGM reference electrode for electrode "A" because they are physically closest to electrode "A." However, in some other implementations, the controller 101 may be configured to eliminate certain electrodes as candidates, for example, based on a "minimum electrode distance." In some implementations, a controller may be configured to calculate a minimum electrode distance based on a measured or assumed tissue conduction velocity (CV) and any electrodes that are positioned within the minimum electrode distance from the electrode of interest can be preemptively eliminated from consideration, such that no electrode is chosen that could be reached by the propagating wave within a given time period. For example, if CV is assumed (or determined by measurement & calculation) to be 1 mm/ms and the unipolar signal duration for the electrode of interest is 10 ms, only electrodes that are more than 10 mm distant from the electrode of interest will be considered. Accordingly, the controller 101 may be configured to select, as the first "candidate" reference electrode, the physically closest electrode that is positioned more than the defined/determined minimum electrode distance from the electrode of interest.

For each electrode, its closest acceptable electrode is chosen (e.g., as described above) and a bipolar EGM is calculated (by subtraction) or measured from the pair. In some implementations, when analyzing the bipolar EGM characteristics for each of these dynamically assigned electrode pairs, measurements are made on the bipolar signal only during a time period surrounding U1 activation (either pre-specified or inside of the measured U1 unipolar signal duration). Because the methods and systems described herein provide electrode pairs that are physically close to each other without concurrent electrical activation, the electrodes in each pair are more likely to be similarly influenced by unrelated signals and noise. Accordingly, using electrode pairs selected by this mechanism to record bipolar electrograms provides improved cancellation of common mode noise shared on both electrodes.

Figure 5:
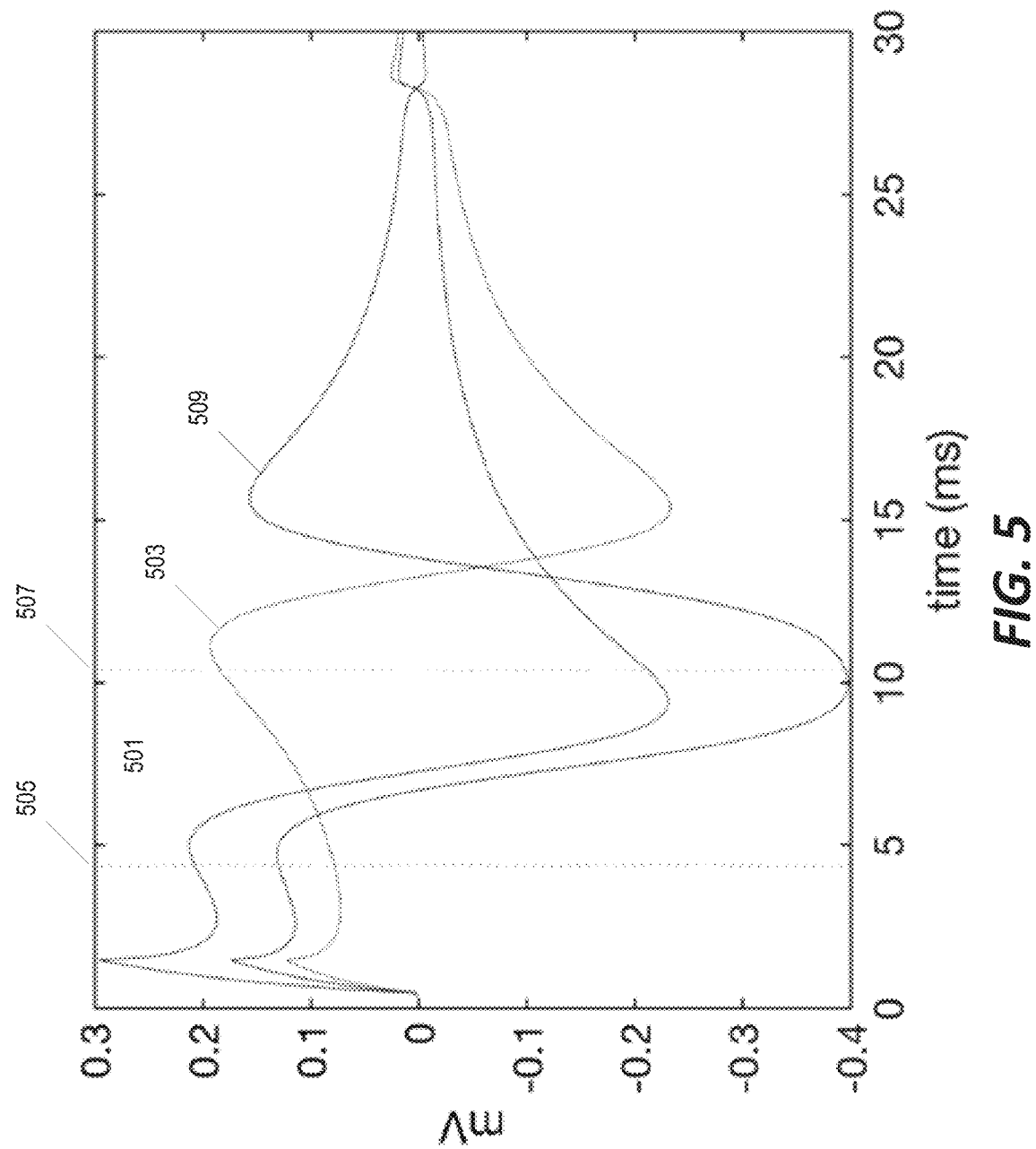
FIG. 5 is a graph of unipolar electrogram signals from two electrodes in the arrangement of FIG. 2 and a bipolar electrogram signal recorded from the same two electrodes.

FIG. 5 illustrates an example of unipolar electrogram signals recorded from two electrodes paired by the methods described above. Signal 501 is the unipolar electrogram for an electrode of interest and signal 503 is the unipolar electrogram for the electrode closest to the electrode of interest that satisfies the pairing criterion/criteria. The local activation time of the electrode of interest is identified in the graph of FIG. 5 by line 505 and the local activation time of the second electrode is identified by line 507. Using the method of FIG. 3 as described above, the second electrode may be confirmed as an appropriate reference electrode for the bipolar electrogram if the time duration between the local activation time 505 and the local activation time 507 exceeds the defined/determined threshold.

Signal 509 in FIG. 5 is the bipolar electrogram signal for the electrode of interest calculated by subtracting the unipolar electrogram signal of the second electrode (signal 503) from the unipolar electrogram signal of the electrode of interest (signal 501). In some implementations, the controller 101 may be configured to calculate bipolar electrogram signal 509 mathematically while separately measuring the unipolar electrogram signals for the two electrodes. However, in other implementations, the controller 101 may be configured to measure the bipolar electrogram directly by operatively controlling various circuit component to provide a measurable signal between the two electrodes.

Figure 6:
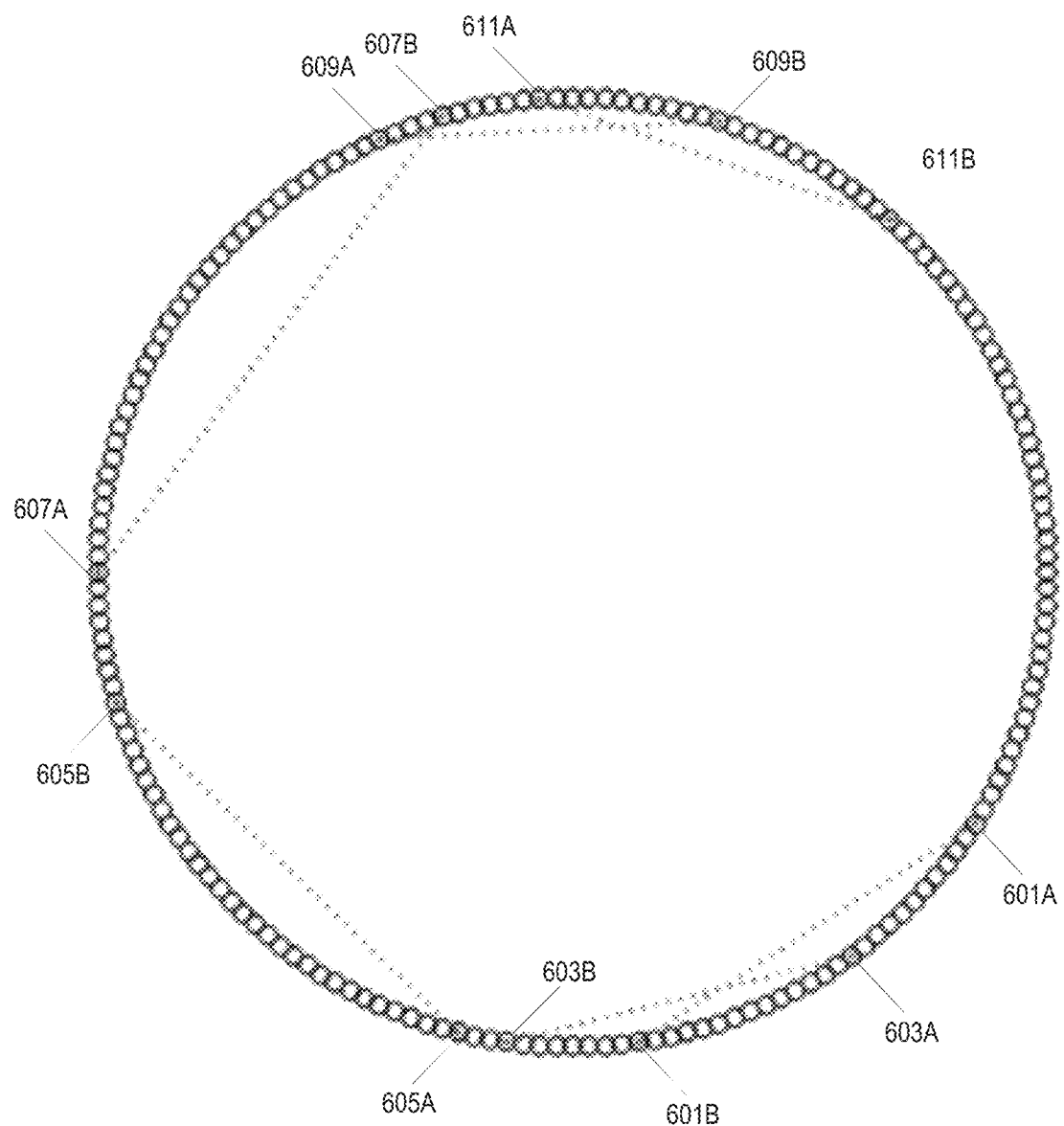
FIG. 6 is a schematic diagram of another example of an electrode arrangement for use in the system of FIG. 1 illustrating examples of electrode pair selections identified using the methods of FIGS. 3 and/or 4.

Finally, FIG. 6 illustrates another example of an electrode configuration that includes a larger quantity of individual electrodes arranged in a ring-shaped array. In this example, unipolar electrograms were simulated at each electrode site as a planar wave-front propagates past them. Using electrode pair suitability criteria, such as described in the examples above, suitable reference electrodes were identified for each of a plurality of different electrodes of interest. The dashed lines show examples of the dynamically assigned electrode parings with electrodes 601A, 603A, 605A, 607A, 609A, and 611A being the electrodes of interest and electrodes 601B, 603B, 605B, 607B, 609B, and 611B being the closest respective electrode to each electrode of interest that satisfied the electrode pair suitability criteria. In particular, in this example, the electrode pairs were selected by identifying the closest electrode to each electrode of interest with an activation time more than 5 ms different from the respective electrode of interest.

Accordingly, the invention provides, among other things, systems and methods for recording bipolar electrogram signals by identifying electrode pairs that are the physically closest electrodes that satisfy at least one selection criterion indicative of an absence of concurrent electrical activation. Various features and advantages of this invention are set forth in the following claims.

What is claimed is:

1. A method for recording a bipolar electrogram, the method comprising:
   positioning a plurality of electrodes at a plurality of different locations relative to cardiac tissue, wherein a position of each electrode of the plurality of electrodes relative to other electrodes of the plurality of electrodes is known;
   selecting an electrode of interest from the plurality of electrodes;
   measuring a unipolar electrogram from the electrode of interest and each electrode of a subset of electrodes, wherein the subset of electrodes includes two or more electrodes of the plurality of electrodes other than the electrode of interest;
   determining, for each electrode of the subset of electrodes, whether the measured unipolar electrogram satisfies at least one selection criterion indicating an absence of concurrent electrical activation of the electrode of interest and the electrode of the subset of electrodes;
   determining, based on the known relative positions of the plurality of electrodes, a physical distance between the electrode of interest and each electrode of the subset of electrodes;
   selecting a second electrode from the subset of electrodes as a bipolar counter electrode for the electrode of interest in response to determining that the measured unipolar electrogram for the second electrode satisfies the at least one selection criterion and that the physical distance between the second electrode and the electrode of interest is less than the physical distance between the electrode of interest and any other electrode of the subset of electrodes that satisfies the at least one selection criterion; and
   sensing and recording the bipolar electrogram for the electrode of interest, wherein sensing the bipolar electrogram for the electrode of interest includes measuring an electrical potential difference between the electrode of interest and the selected second electrode.

2. The method of claim 1, further comprising determining, based on the measured unipolar electrogram for the electrode of interest, a local activation time for the electrode of interest, and
   wherein determining, for each electrode of the subset of electrodes, whether the recorded unipolar electrogram satisfies the at least one selection criterion includes:

determining a local activation time for the electrode of the subset of electrodes based on the measured unipolar electrogram for the electrode of the subset of electrodes, determining a local activation time difference as a difference between the local activation time for the electrode of interest and the local activation time for the electrode of the subset of electrodes, and determining that the at least one selection criterion is satisfied in response to determining that the local activation time difference exceeds a time difference threshold.

3. The method of claim 1, further comprising:

determining, based on the measured unipolar electrogram for the electrode of interest, a local activation time for the electrode of interest; and determining, based on the measured unipolar electrogram for the electrode of interest, a unipolar signal amplitude of the measured unipolar electrogram for the electrode of interest at the local activation time for the electrode of interest, and wherein determining, for each electrode of the subset of electrodes, whether the measured unipolar electrogram satisfies the at least one selection criterion includes determining, based on the measured unipolar electrogram for the electrode of the subset of electrodes, a unipolar signal amplitude of the electrode of the subset of electrodes at the local activation time for the electrode of interest, and determining that the at least one selection criterion is satisfied based on an amplitude difference between the unipolar signal amplitude of the electrode of the subset of electrodes at the local activation time for the electrode of interest and the unipolar signal amplitude of the electrode of interest at the local activation time for the electrode of interest.

4. The method of claim 3, wherein determining that the at least one selection criterion is satisfied based on the amplitude difference includes calculating the amplitude difference, and determining that the at least one selection criterion is satisfied in response to determining that the amplitude difference exceeds an amplitude difference threshold.

5. The method of claim 1, further comprising selecting the subset of electrodes from the plurality of electrodes by selecting electrodes that are each positioned beyond a minimum electrode distance from the electrode of interest, wherein the minimum electrode distance is indicative of a tissue conduction velocity.

6. The method of claim 1, wherein positioning the plurality of electrodes includes positioning an electrode catheter including the plurality of electrodes such that each electrode of the plurality of electrodes contacts a different tissue location, wherein each electrode of the plurality of electrodes is coupled to the electrode catheter at a known fixed position relative to the other electrodes of the plurality of electrodes.

7. The method of claim 1, further comprising outputting a visual indication of the sensed bipolar electrogram on a display screen.

8. A method for recording a bipolar electrogram, the method comprising:

positioning a plurality of electrodes at a plurality of different locations relative to cardiac tissue, wherein a position of each electrode of the plurality of electrodes relative to other electrodes of the plurality of electrodes is known;

selecting an electrode of interest from the plurality of electrodes;

defining a sequence of candidate electrodes from the plurality of electrodes in increasing order of distance between each candidate electrode and the electrode of interest;

measuring a unipolar electrogram from the electrode of interest;

iteratively measuring a unipolar electrogram from each candidate electrode in the sequence of candidate electrodes and evaluating whether the measured unipolar electrogram from the candidate electrode satisfies at least one selection criterion indicating an absence of concurrent electrical activation of the electrode of interest and the candidate electrode;

selecting, as a second electrode, a first candidate electrode in the sequence of candidate electrodes with a measured unipolar electrogram that satisfies the at least one selection criterion; and sensing and recording the bipolar electrogram for the electrode of interest, wherein sensing the bipolar electrogram for the electrode of interest includes measuring an electrical potential difference between the electrode of interest and the selected second electrode.

9. The method of claim 8, wherein defining the sequence of candidate electrodes includes including an electrode from the plurality of electrodes as a candidate electrode in response to determining, based on the known relative positions of the plurality of electrodes, that a physical distance between the electrode and the electrode of interest exceeds a minimum electrode distance, wherein the minimum electrode distance is indicative of a tissue conduction velocity.

10. The method of claim 8, further comprising outputting a visual indication of the sensed bipolar electrogram on a display screen.

11. A bipolar electrogram recording system comprising:

a plurality of electrodes positionable at each of a plurality of different locations relative to cardiac tissue, wherein a position of each electrode of the plurality of electrodes relative to other electrodes of the plurality of electrodes is known;

a memory, wherein the memory stores known relative position information for the plurality of electrodes; and an electronic controller communicatively couplable to the plurality of electrodes and configured to select an electrode of interest from the plurality of electrodes, measure a unipolar electrogram from the electrode of interest and from each electrode of a subset of electrodes, wherein the subset of electrodes includes two or more electrodes of the plurality of electrodes other than the electrode of interest, determine, for each electrode of the subset of electrodes, whether the measured unipolar electrogram satisfies at least one selection criterion indicating an absence of concurrent electrical activation of the electrode of interest and the electrode of the subset of electrodes, determine, based on the known relative position information stored on the memory of the electronic controller, a physical distance between the electrode of interest and each electrode of the subset of electrodes, select a second electrode from the subset of electrodes as a bipolar counter electrode for the electrode of interest in response to determining that the measured unipolar electrogram for the second electrode satisfies the at least one selection criterion and that the physical distance between the second electrode and the electrode of interest is less than a physical distance between the electrode of interest and any other electrode of the subset of electrodes that satisfies the at least one selection criterion; and sense and record to the memory a bipolar electrogram for the electrode of interest, wherein sensing the bipolar electrogram for the electrode of interest includes measuring an electrical potential difference between the electrode of interest and the selected second electrode.

12. The bipolar electrogram recording system of claim 11, wherein the electronic controller is further configured to determine a local activation time for the electrode of interest based on the measured unipolar electrogram for the electrode of interest, and wherein the electronic controller is configured to determine, for each electrode of the subset of electrodes, whether the recorded unipolar electrogram satisfies the at least one selection criterion by:

determining a local activation time for the electrode of the subset of electrodes based on the measured unipolar electrogram for the electrode of the subset of electrodes, determining a local activation time difference as a difference between the local activation time for the electrode of interest and the local activation time for the electrode of the subset of electrodes, and determining that the at least one selection criterion is satisfied in response to determining that the local activation time difference exceeds a time difference threshold.

13. The bipolar electrogram recording system of claim 11, wherein the electronic controller is further configured to:

determine a local activation time for the electrode of interest based on the measured unipolar electrogram for the electrode of interest, and determine a unipolar signal amplitude of the measured unipolar electrogram for the electrode of interest at the local activation time for the electrode of interest, wherein the electronic controller is configured to determine, for each electrode of the subset of electrodes, wherein the measured unipolar electrogram satisfies the at least one selection criterion by determining a unipolar signal amplitude of the measured unipolar electrogram from the electrode of the subset of electrodes at the local activation time for the electrode of interest, and determining that the the at least one selection criterion is satisfied based on an amplitude different between the unipolar signal amplitude of the electrode of the subset of electrodes at the local activation time for the electrode of interest and the unipolar signal amplitude of the electrode interest at the local activation time for the electrode of interest.

14. The bipolar electrogram recording system of claim 13, wherein the electronic controller is configured to determine that the at least one selection criterion is satisfied based on the amplitude difference by calculating the amplitude difference, and determining that the at least one selection criterion is satisfied in response to determining that the amplitude difference exceeds an amplitude difference threshold.

15. The bipolar electrogram recording system of claim 11, wherein the electronic controller is further configured to define a sequence of candidate electrodes from the plurality of electrodes in increasing order of distance between each candidate electrode and the electrode of interest, wherein the sequence of candidate electrodes includes the subset of electrodes, wherein the electronic controller is configured to determine, for each electrode of the subset of electrodes, whether the measured unipolar electrogram satisfies the at least one selection criterion by iteratively evaluating whether each candidate electrode in the sequence of candidate electrodes satisfies the at least one selection criterion, and wherein the electronic controller is configured to select the second electrode from the subset of electrodes as the bipolar counter electrode for the electrode of interest by further selecting, as the bipolar counter electrode for the electrode of interest, a first candidate electrode in the sequence of candidate electrodes that satisfies the at least one selection criterion.

16. The bipolar electrogram recording system of claim 15, wherein the electronic controller is configured to define the sequence of candidate electrodes by including an electrode from the plurality of electrodes as a candidate electrode in response to determining that the physical distance between the electrode and the electrode of interest exceeds a minimum electrode distance, wherein the minimum electrode distance is indicative of a tissue conduction velocity.

17. The bipolar electrogram recording system of claim 11, wherein the electronic controller is further configured to select the subset of electrodes by selecting electrodes that are each positioned beyond a minimum electrode distance from the electrode of interest, wherein the minimum electrode distance is indicative of a tissue conduction velocity.

18. The bipolar electrogram recording system of claim 11, further comprising an electrode catheter, wherein the electrode catheter includes the plurality of electrodes fixedly arranged on the electrode catheter, and wherein the memory stores data indicative of a relative position of each electrode on the electrode catheter.

19. The bipolar electrogram recording system of claim 18, wherein the plurality of electrodes are arranged in a ring pattern on the electrode catheter.

20. The bipolar electrogram recording system of claim 11, further comprising a display screen communicatively coupled to the electronic controller, wherein the electronic controller is configured to cause the display screen to output a visual indication of the sensed bipolar electrogram.

* * * * *